United States Patent [19]

Platzek et al.

[11] Patent Number: 5,676,926
[45] Date of Patent: Oct. 14, 1997

[54] PROCESS FOR THE PRODUCTION OF DTPA-TETRAESTERS OF TERMINAL CARBOXYLIC ACIDS

[75] Inventors: Johannes Platzek; Ulrich Niedballa; Bernd Radeuchel, all of Berlin, Germany

[73] Assignee: Schering Aktiengesellschaft, Berlin, Germany

[21] Appl. No.: 634,186

[22] Filed: Apr. 18, 1996

Related U.S. Application Data

[62] Division of Ser. No. 461,007, Jun. 5, 1995, Pat. No. 5,514,810.

[30] Foreign Application Priority Data

Feb. 21, 1995 [DE] Germany .................. 195 08 058.0

[51] Int. Cl.[6] .................................................. C07C 229/06
[52] U.S. Cl. .......................... 424/9.3; 424/9.4; 514/533; 514/547; 514/548; 560/38; 560/39; 560/40; 560/169
[58] Field of Search .................................... 560/38, 39, 40, 560/169; 424/9.3, 9.4

[56] References Cited

FOREIGN PATENT DOCUMENTS

| 71564 B1 | of 0000 | European Pat. Off. . |
|---|---|---|
| 0 353 350 | 2/1990 | European Pat. Off. . |
| 0592306 | 4/1994 | European Pat. Off. . |
| 32 21 026 | 12/1987 | Germany . |

OTHER PUBLICATIONS

Williams et al., *J. Org. Chem.*, 58, 1151–1158 (1993).
C.F. Ward, *Soc.*, 121: 1164 (1922).

*Primary Examiner*—Joseph Conrad
*Attorney, Agent, or Firm*—Millen, White, Zelano & Branigan, P.C.

[57] ABSTRACT

The invention relates to a process for the production of diethylenetriaminepentacarboxylic acid tetraesters of general formula I

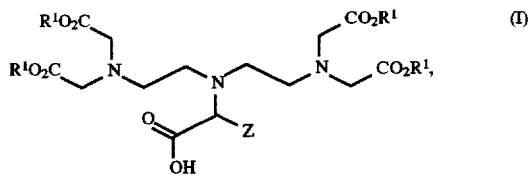

in which $R^1$ and Z have different meanings.

1 Claim, No Drawings

PROCESS FOR THE PRODUCTION OF DTPA-TETRAESTERS OF TERMINAL CARBOXYLIC ACIDS

This is a division of application Ser. No. 08/461,007, filed Jun. 5, 1995, now U.S. Pat. No. 5,514,810.

BACKGROUND OF THE INVENTION

The invention relates to a process for the production of diethylenetriaminepentacarboxylic acid tetraesters of terminal carboxylic acids as well as the use of compounds, produced by the described process, for the production of agents for NMR, x-ray and radiodiagnosis as well as radiotherapy.

Diethylenetriaminepentaacetic acid (DTPA) and derivatives of this compound are widely used in medicine and technology, both in free form and in the form of their complex compounds. In EP 71564 B1, i.a., the meglumine salt of the gadolinium(III) complex of diethylenetriaminepentaacetic acid (DTPA) is described as a contrast medium for NMR tomography. A preparation which contains this complex was approved worldwide under the name Magnevist® as the first NMR contrast medium. After intravenous administration, this contrast medium spreads extracellularly and is excreted renally by glomerular secretion. A passage of intact cell membranes is practically not observed. Magnevist® is especially well-suited for the visualization of pathological areas (e.g., inflammations, tumors).

In the past, there have been many attempts to link DTPA with functional radicals which exhibit an organ or cell specificity to achieve in this way a contrast medium concentration in certain types of tissue.

A DTPA derivative, which is suitable to be used as starting substance for the regioselective linkage of the central carboxylic acid of the DTPA derivative to an amine-containing radical, which has the above-mentioned properties, was described by Rapoport (J. Org. Chem., 58, 1151 (1993)). But the process for the production of this tetraester indicated in this bibliographic reference is affected by the drawback that it uses an amino acid as starting material. Thus, the possible substitution models of the products of this process are limited to the substitution models of the available amino acids. There is therefore a need for a process which avoids this drawback and allows the production of compounds with substituents, which do not occur in amino acids. The object of the invention thus is to make available such a process. The achievement of this object is performed by the object characterized in the claims.

It has been found that the process for the production of diethylenetriaminepentacarboxylic acid tetraesters of general formula (I)

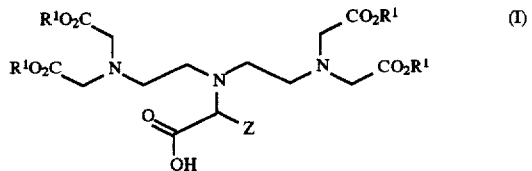

in which $R^1$ stands for a tert-butyl group or a benzyl group, and

Z stands for hydrogen or for a saturated or unsaturated, branched or straight-chain $C_1$–$C_{50}$ alkyl chain, in which the chain or parts of this chain optionally can form a cyclic $C_5$–$C_8$ unit or a bicyclic $C_{10}$–$C_{14}$ unit, which contains 0 to 10 oxygen and/or 0 to 2 sulfur atoms and/or 0 to 3 carbonyl, 0 to 1 thiocarbonyl, 0 to 2 imino, 0 to 2 phenylene, 0 to 1 3-indole, 0 to 1 methyl-imidazol-4-yl and/or 0 to 3 N—$R^3$ groups and is substituted by 0 to 2 phenyl, 0 to 2 pyridyl, 0 to 5 $R^2O$, 0 to 1 HS, 0 to 4 $R^2OOC$, 0 to 4 $R^2OOC$—$C_{1-4}$ alkyl and/or 0 to 1 $R^2(H)N$ groups in which optionally present aromatic groups can be substituted zero to five times, independently of one another, by fluorine, chlorine, bromine, iodine, $R^2O_2C$, 4 $R^2OOC$—$C_{1-4}$ alkyl, $R^2(H)N$, $R^2NHOC$, $R^2CONH$, $O_2N$, $R^2O$, $R^2$ groups, and in which $R^2$ stands for hydrogen or a branched or unbranched $C_1$–$C_4$ alkyl radical, characterized in that a compound of general formula II

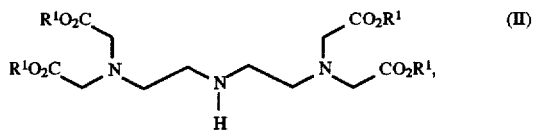

in which $R^1$ has the above-indicated meaning, is reacted with a carboxylic acid ester of general formula III

in which Z' has the meaning of an optionally protected group Z, in which Z has the above-indicated meaning and $T^1$ stands for a straight-chain or branched $C_1$–$C_6$ alkyl group, a benzyl, trimethylsilyl, triisopropylsilyl, 2,2,2-trifluoroethoxy, 2,2,2-trichloroethoxy group or a metal ion equivalent of an alkali or alkaline-earth element, in which $T^1$ is always different from $R^1$, and Nu stands for a nucleofuge and then, by cleavage of group $T^1$ as well as of protective groups optionally contained in Z', the free acid of general formula I is produced, is surprisingly excellently suited to overcome the drawbacks of the known processes.

The invention therefore relates to the process for the production of compounds of general formula I.

The designations of terminal or central carboxylic acids can be defined as follows:

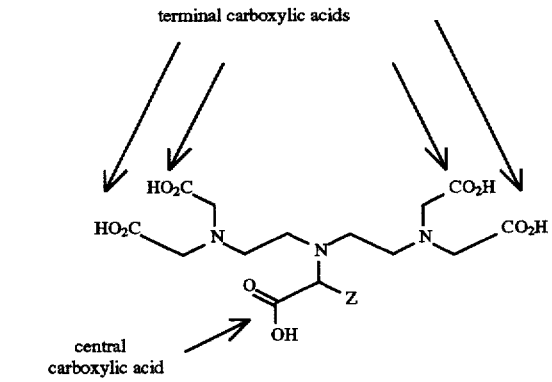

As radicals Z, there can be mentioned as examples the methyl, ethyl, n-propyl, i-propyl, n-butyl, i-butyl, pentyl, hex-3-enyl, heptyl, octyl, i-octyl, cyclopentyl, cyclohexyl, cycloheptyl, cyclooctyl, phenyl or benzyl radical; as well as radicals of formulas

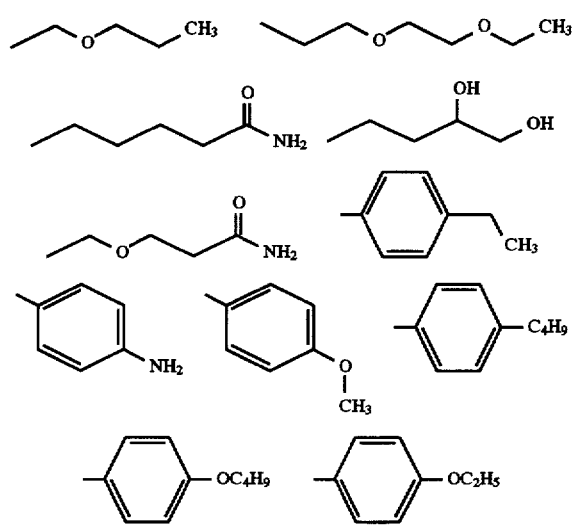

Radical Z can contain, for example, also a heteroaromatic compound, such as a 3-indole radical and/or a histidine radical.

Preferred radicals Z are the methyl, ethyl, propyl, i-propyl, butyl, i-butyl, *tert*-butyl, pentyl, hexyl, cyclohexyl, hydroxymethyl, 1-hydroxyethyl, carboxymethyl, 2-carboxyethyl, 4-aminobutyl, mercaptomethyl, methylthiomethyl, p-hydroxyphenyl or p-hydroxybenzyl radicals of the phenyl and the benzyl radicals.

The HOOC, $H_2N$, HS or HO groups optionally present in Z can in this case be present in protected form. Details of the protective group syntheses are further summarized below.

The reaction of compounds of general formula II with compounds of general formula III according to the invention takes place in polar solvents, such as dimethylformamide, acetonitrile, tetrahydrofuran, 1,4-dioxane, formamide, dimethylacetamide, dimethyl sulfoxide, acetone as well as in alcohols, such as, for example, methanol, ethanol, isopropanol, preferably in acetonitrile and dimethylformamide. In the case of preferred bromides and chlorides, catalytic amounts of iodide can be added. To catch the acid that has developed in the alkylation, organic bases, such as, e.g., triethylamine, Hünig base or 1,4-diazabicyclooctane (DABCO) or else metal hydrides, for example, sodium hydride or alkali or alkaline-earth hydroxides or their carbonates, are used. Preferably, potassium carbonate is used. The reactions take place at 0°–100° C., preferably between 20° and 60° C. The alkylation reagents described by general formula III are partially commercially available or can be produced from the corresponding carboxylic acids, or α-hydroxycarboxylic acids in a way known in the literature (see, for example: C. F. Ward, Soc., 121: 1164 (1922)).

The subsequent release and isolation of the compounds of general formula I takes place in that the intermediately occurring compound of general formula Ia

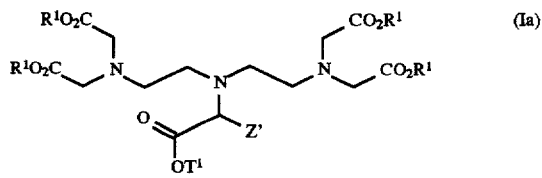

in which $R^1$ and $T^1$ have the above-indicated meaning and $Z^1$ has the meaning of an optionally protected group Z, in which Z has the above-indicated meaning, is converted by cleavage of group $T^1$ as well as of the protective groups optionally contained in Z to the compound of general formula I. Preferred radical $T^1$ is the benzyl radical, if $R^1$ stands for a *tert*-butyl group.

The cleavage of protective group $T^1$ as well as the cleavage of the protective groups optionally contained in Z' (conversion of radical Z' to Z) from compounds of general formula Ia takes place according to the processes known to one skilled in the art, such as, for example, by hydrolysis, hydrogenolysis, acid or alkaline saponification of the esters in aqueous-alkaline medium, and optionally solubilizers, such as alcohols, preferably methanol, ethanol, isopropanol or ethers, such as tetrahydrofuran, 1,4-dioxane, 1,2-dimethoxyethane, can be added. As a base, alkali or alkaline-earth hydroxides (such as, e.g., lithium hydroxide, sodium hydroxide or barium hydroxide) or alkali or alkaline-earth carbonates (such as, e.g., potassium carbonate and cesium carbonate) can be used. Preferred temperatures are 0°–100° C., especially 0°–50° C. The subsequent isolation of the compound of general formula I takes place so that it is reacted with ammonium salts, such as, e.g., $NH_4Cl$, $(NH_4)_2SO_4$ or $(NH_4)_3PO_4$ or the salts are converted to free acids with acid ion exchanger.

Also, the use of diluted citric acid or ion exchangers in $H^+$ form has proven itself for the release of the acid group from the alkali or alkaline-earth salts. The acid saponification is performed with mineral acids, such as, e.g., hydrochloric acid, sulfuric acid or else also organic acids (e.g., trifluoroacetic acid) at temperatures of 0°–100° C., preferably 0°–50° C., in the case of trifluoroacetic acid between 0°–25° C. The cleavage of silyl esters takes place with the help of fluoride ions.

The hydrogenolytic cleavage of benzyl derivatives takes place by using the palladium catalysts known to one skilled in the art, preferably 10% palladium on activated carbon or Pearlman's catalyst $Pd(OH)_2$ on carbon. Homogeneous catalysts of the Wilkinson catalyst type can also be used. The hydrogenation is performed in alcohols, such as methanol, ethanol or isopropanol, but preferably isopropanol at temperatures between 10°–50° C., but preferably at room temperature and normal pressure.

Advantages of the Process According to the Invention

Relative to the process described by Rapoport (J. Org. Chem., 58, 1151 (1993)), the process according to the invention exhibits the advantage that it is not limited to amino acids as starting material. Thus, radical Z, influencing the stability of complex compounds, is not limited to those radicals that occur in amino acids. Moreover, by the free selection of radical Z, the process makes possible the production of compounds with a given pharmacological profile.

Production of the Starting Compounds

The compound of general formula II is obtained by cleavage of protective group A from the compound of general formula IV

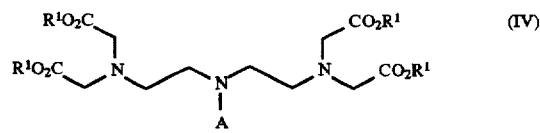

in which $R^1$ is in the above-mentioned meaning and

A stands for a protective group, such as, for example, a benzyloxycarbonyl, *tert*-butyloxycarbonyl (BOC), fluorenylmethoxycarbonyl (FMOC), benzyl, 4-methoxybenzyl, $(CH_3)_3Si$—$(CH_2)_2$—$SO_2$, $CF_3CO$, $CCl_3CO$, $(C_6H_5)(\textit{tert}\text{-Bu})_2Si$ or a trityl group.

The cleavage takes place, if A is the BOC radical, by treatment with trifluoroacetic acid. Silyl protective groups are cleaved off with diluted mineral acid or with fluoride ions. If A means the $(CH_3)_3Si$—$(CH_2)_2$—$SO_2$ group, tetrabutylammonium fluoride is used as cleavage reagent. If A represents the benzyl radical or the benzyloxycarbonyl radical, the latter is cleaved off by hydrogenolysis with palladium catalyst (10% Pd/C) or more advantageously with Pearlman's catalyst $(Pd(OH)_2/C)$ in alcohols, preferably ethanol, at room temperature.

The compound of general formula IV is obtained from the compound of general formula V

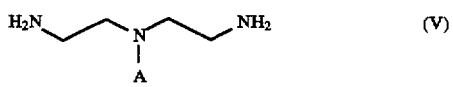

in which

A is in the above-mentioned meaning, by reaction with α-haloacetic acid esters.

The compound of general formula V, in which A represents the benzyl radical, can also be reacted by reaction of benzylamine with the alkylation reagent of general formula VI

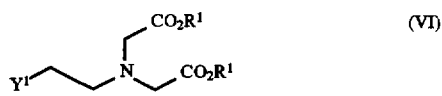

in which $R^1$ has the above-indicated meaning and $Y^1$ stands for a halogen atom, such as Cl, Br or I, but preferably Cl.

The reaction of compound (V) with compound (VI) takes place preferably in a buffered alkylation reaction, in which an aqueous phosphate buffer solution is used as buffer. The reaction takes place at pH 7–9, but preferably at pH 8. The buffer concentration can be between 0.1 and 2.5M, but a 2M phosphate-buffer solution is preferred. The temperature of the alkylation can be between 0° and 50° C., the preferred temperature is room temperature.

The reaction is performed in a polar solvent, such as, e.g., acetonitrile, tetrahydrofuran, 1,4-dioxane, or 1,2-dimethoxyethane. Acetonitrile preferably is used.

If $Y^1$ in general formula VI is a Cl or Br atom, an alkali iodide, such as, e.g., Na, KI, can be added to the reaction in catalytic amounts.

The structural element of general formula VI used in the alkylation can be produced if $Y^1$ stands for bromine, according to the description of Rapoport (M. A. Williams, H. Rapoport, J. Org. Chem., 58, 1151 (1993)). But the corresponding compound with $Y^1$=Cl can be used in the same way for the above-described reaction. In addition, the chlorine compound can be produced economically from the alcohol of general formula VII, in which $R^1$ represents the benzyl or *tert*-butyl group,

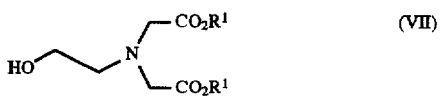

by reaction with thionyl chloride.

The compound of general formula V is produced by a cleavage of protective group L, known to one skilled in the art, from the compound of general formula VIII

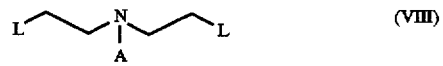

in which

A has the above-mentioned meaning and in which

L stands for a group —NHD, in which

D represents, e.g., the benzyloxycarbonyl, BOC, $CF_3CO$, $Cl_3CCO$ or the trityl group or L stands for a phthalimido group.

If D stands for the benzyloxycarbonyl group, a hydrogenolysis in the presence of palladium catalysts takes place (see above).

If D is the $CF_3CO$ group, a saponification is performed with alkali or alkaline-earth hydroxides or their carbonates, but preferably potassium carbonate. Aqueous ammonia solution can also be used. As solvent, preferably mixtures of alcohols or tetrahydrofuran or 1,4-dioxane with water are used. The reaction temperatures are between 0°–60° C., the reaction is performed preferably at room temperature. If L is the phthalimido group, the cleavage of the phthalyl protective group takes place by hydrazinolysis or by treatment with alkali hydroxides, preferably sodium hydroxide or potassium hydroxide in aqueous alcohols, preferably n-butanol with refluxing or by treatment with aqueous mineral acids, preferably concentrated hydrochloric acid, with refluxing.

It has proven especially advantageous to undertake the saponification of the $CF_3$—CO groups with aqueous potassium carbonate solution, since the alkylation to tetraesters of general formula IV can be performed in this way without isolation of the intermediate stage of general formula V.

1,4,7-Triaza-4-benzyl-heptane can also be produced as described in EP 0292689.

The compound of general formula VIII can be obtained by reaction of the compound of general formula IX

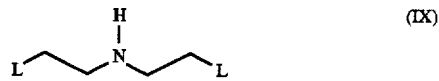

in which

L stands for the group —NHD, with D in the above-indicated meaning, or stands for a phthalimido group, with the standard protective group reagents (see, e.g., Protective Groups in Organic Syntheses, Second Edition, T. W. Greene and P. G. M. Wuts, John Wiley & Sons, Inc., New York, 1991).

The compounds of general formula IX are obtained by reaction of an acylation reagent of general formula X

with diethylenetriamine (XI)

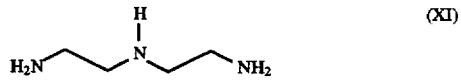

in which

G stands for a C=N group or an $OR^3$ group, $R^3$ stands for a branched or unbranched, completely or partially fluorinated $C_1$–$C_6$ alkyl group or a benzyl group or if L represents the phthalimino group, D—G stands for phthalic anhydride.

Preferred reagents D—G are, in addition to the mentioned phthalic anhydride, trifluoroacetic acid ethyl ester and cyanobenzyl formate.

Thus, the reaction of diethylenetriamine (XI) with trifluoroacetic acid ethyl ester in ethanol at room temperature produces in almost quantitative yield the already known (U.S. Pat. No. 4,415,737 A (1983)) 1,7-bis-trifluoroacyl derivative (see examples).

The 1,7-dibenzyloxycarbonyl compound (see examples) can be obtained by reaction of triamine (XI) with cyanobenzyl formate in tetrahydrofuran (Shun-Ichi Munehashi et al., Chemistry Letters, pp. 879–882 (1987)).

The phthalimido protective group can, as described in J. Org. Chem. USSR, 23:3302 (1987), be introduced in diethylenetriamine (XI).

Protective Groups

The protection of the designated groups in radical Z can take place with numerous possibilities known to one skilled in the art. The embodiments described below are used in explanation of these protective group techniques without being limited to these synthesis methods.

As acid protective groups, $C_1$–$C_6$ alkyl, $C_6$–$C_{10}$ aryl and $C_6$–$C_{10}$—Ar($C_1$–$C_4$) alkyl groups as well as trialkylsilyl groups are suitable. Preferred are the methyl, ethyl, propyl, isopropyl, n-butyl, i-butyl and the *tert*-butyl groups.

The cleavage of these acid protective groups takes place according to the processes known to one skilled in the art, for example by hydrolysis, hydrogenolysis, alkaline saponification of the esters with alkali in aqueous-alcoholic solution at temperatures of 0° to 50° C., acid saponification with mineral acids or, in the case of *tert*-butyl esters, with the help of trifluoroacetic acid.

As hydroxy protective groups, e.g., benzyl, 4-methoxybenzyl, 4-nitrobenzyl, trityl, diphenylmethyl, trimethylsilyl, dimethyl-*tert*-butylsilyl or diphenyl-*tert*-butylsilyl groups are suitable.

The hydroxy groups can also be present, e.g. as THP-ether, α-alkoxyethylether, MEM-ether or as esters with aromatic or aliphatic carboxylic acids, such as, e.g., acetic acid or benzoic acid. In the case of polyols, the hydroxy groups can also be protected in the form of ketals with, e.g., acetone, acetaldehyde, cyclohexanone or benzaldehyde.

The hydroxy protective groups can be released according to the methods in the literature known to one skilled in the art, e.g., by hydrogenolysis, acid treatment of the ethers and ketals, alkali treatment of esters or treatment of silyl protective groups with fluoride (see, e.g., Protective Groups in Organic Syntheses, Second Edition, T. W. Greene and P. G. M. Wuts, John Wiley & Sons, Inc., New York, 1991).

The thiol groups can be protected as benzyl ethers, which can be cleaved with sodium in ammonia or boiling ethanol (W. I. Patterson, v. du Vigneaud, J. Biol. Chem. 111:393, 1993). S-*tert*-butyl ethers can be readily cleaved with hydrogen fluoride/anisole at room temperature (S. Salzakibona et al., Bull. Chem. Soc., Japn., 40:2164, (1967)). S-benzyloxycarbonyl derivatives can be easily cleaved by concentrated ammonia solution at room temperature (A. Berger et al., J. Am. Chem. Soc. 78:4483, 1956). S-benzyloxycarbonyl derivatives of trifluoroacetic acid are cleaved only at boiling temperature (L. Zervas et al., J. Am. Chem. Soc., 85:1337 (1963)).

The $NH_2$ groups can be protected and again opened in varied ways. The N-trifluoroacetyl derivative is cleaved by potassium carbonate or sodium carbonate in water (H. Newman, I. Org. Chem., 30:287 (1965), M. A. Schwartz et al., J. Am. Chem. Soc., 95, G12 (1973)) or singly cleaved by ammonia solution (M. Imazama and F. Eckstein, J. Org. Chem., 44:2039 (1979)). Also, the *tert*-butyloxycarbonyl derivative is equally easy to cleave: stirring with trifluoroacetic acid is sufficient (B. F. Lundt et al., J. Org. Chem., 43:2285 (1978)).

The group of $NH_2$ protective groups to be cleaved hydrogenolytically or reductively is very large: the N-benzyl group can be cleaved easily with hydrogen/Pd—C (W. H. Hartung and R. Simonoff, Org. Reactions VII, 263 (1953)), which also applies for the trityl group (L. Zervas et al., J. Am. Chem. Soc., 78:1359 (1956)) and the benzyloxycarbonyl group (M. Bergmann and L. Zervas, Ber. 65:1192 (1932)).

Of the silyl derivatives, the easily cleavable *tert*-butyldiphenylsilyl compounds (L. E. Overman et al., Tetrahedron Lett., 27:4391 (1986)), as also the 2-(trimethylsilyl)-ethyl carbamates (L. Grehn et al., Angew. Chem. [Applied Chemistry] Int. Ed. Engl., 23:296 (1983)) and the 2-trimethylsilylethanesulfonamides (R. S. Garigipati and S. M. Weinreb, J. Org. Chem., 53:4143 (1988)), are used, which can be cleaved with fluoride ions. Especially easily cleavable is the 9-fluorenylmethyl-carbamate: the cleavage takes place with amines such as piperidine, morpholine, 4-dimethylaminopyridine, but also with tetrabutylammonium fluoride (L. A. Corpino et al., J. Org. Chem., 55:1673 (1990), M. Ueki and M. Amemiya, Tetrahedron Lett., 28:6617 (1987)).

Use of the Process Products

The compounds of general formula I produced according to the process of the invention can be used for the following purposes:

1. The compounds can be coupled by the free acid group regioselectively to functional radicals. As amines in this case, monoamines, oligoamines and polyamines are possible (e.g., octadecylamine, 1,3,6,9 tetraazacyclododecylamine, polylysine or insulin). After cleavage of groups $R^1$, the DTPA amides that have developed can be used as complexing agents for the production of x-ray, NMR and radiodiagnostic agents or radiotherapeutic agents. The selection of possible radical $R^1$ makes possible a cleavage under mild (acid or neutral) conditions. In this way, sensitive conjugates can be formed with peptides, hormones or antibodies.

2. After cleavage of groups $R^1$, the complexing agents that have developed can also be used as an antidote for detoxification with inadvertent incorporation of heavy metals and/or their radioactive isotopes. Here, they are used in the form of free complexing agents and/or the salts of the complexing agents with physiologically compatible cations.

3. After cleavage of groups $R^1$, the complexing agents that have developed can also be used directly for the production of x-ray, NMR and radiodiagnostic agents or radiotherapeutic agents.

The cleavage of protective groups $R^1$ takes place in each case according to the processes known to one skilled in the art, for example by hydrolysis, hydrogenolysis, alkaline saponification of esters with alkali in aqueous-alcoholic solution at temperatures of 0° to 50° C., acid saponification with mineral acids or, in the case of *tert*-butyl esters, with the help of trifluoroacetic acid. Preferred are the hydrogenolytic cleavage of the benzyl group and the saponification of the

*tert*-butyl group with trifluoroacetic acid, since the latter take place in an especially mild way. Amides are not saponified by this type of cleavage and changes of the functional radicals optionally present in Z do not occur.

The production of complexes for the production of NMR or x-ray diagnostic agents can take place in the way in which it was disclosed in Patents EP 71564, EP 130934 and DE-OS 3401052. To this end, the metal oxide or a metal salt (for example, a chloride, nitrate, acetate, carbonate or sulfate) of the element of atomic numbers 21–32, 37–39, 42–44 or 57–83 is dissolved or suspended in water and/or a lower alcohol (such as methanol, ethanol or isopropanol) and reacted with the solution or suspension of the equivalent mount of the complexing agent according to the invention.

If the complexing agents are to be used for the production of radiodiagnostic agents or radiotherapeutic agents, the production of the complexes from the complexing agents can take place according to the methods described in "Radiotracers for Medical Applications," Vol. I, CRC Press, Boca Raton, Fla.

For the production of pharmaceutical agents, the methods described in DE 4302287 A1 can be used. Details of use and dosage can also be found in this laid-open specification as well in the literature cited there.

The invention therefore also relates to the use of the compounds, produced by the process according to the invention, for the production of pharmaceutical agents, especially for the production of contrast media for NMR and x-ray diagnosis.

In general, it has been possible to provide a process which makes possible the synthesis of new complexing agents, which open up new possibilities in diagnostic and therapeutic medicine.

The following examples are used for a more detailed explanation of the object of the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German patent application 195 08 058.0, is hereby incorporated by reference.

EXAMPLES

Example 1

3,9-Bis(tert-butoxycarbonylmethyl)-3,6,9-triazaundecanedioicacid-di-tert-butyl ester a) 1,7-Bis(trifluoroacetyl)-1,4,7-triazaheptane 113.3 g (790 mmol) of trifluoroacetic acid ethyl ester is instilled in a solution of 41.14 g (390 mmol) of 1,4,7-triazaheptane in 350 ml of tetrahydrofuran at 0° C. and under nitrogen. It is allowed to stir overnight at room temperature, concentrated by evaporation in a vacuum. The remaining oil is crystallized from hexane.

Yield: 115 g (99.9% of theory) Melting point: 68°–70° C. Elementary analysis: Cld: C 32.55 H 3.76 F 38.62 N 14.24 Fnd: C 32.63 H 3.75 F 38.38 N 14.19 b) 1,7-Bis(trifluoroacetyl)-4-benzyloxycarbonyl-1,4,7-triazaheptane 14.75 g (50 mmol) of the trifluoroacetyl compound produced under Example 1a) as well as 8.3 ml (60 mmol) of triethylamine are dissolved in 120 ml of dichloromethane and cooled to 0° C. 7.5 ml (53 mmol) of benzyl chloroformate (97%), dissolved in 20 ml of dichloromethane, is now instilled with stirring. It is allowed to stir overnight at room temperature, the salts are extracted with distilled water, the dichloromethane Solution is dried on sodium sulfate, evaporated to dryness in a vacuum and the residue from ether/hexane is crystallized.

Yield: 18.40 g (85.7% of theory) Melting point: 131°–32° C. Elementary analysis: Cld: C 44.76 H 3.99 F 26.55 N 9.79 Fnd: C 44.87 H 4.03 F 26.62 N 9.61 c) 3,9-Bis(tert-butoxycarbonylmethyl)-6-benzyloxycarbonyl-3,6,9-triazaundecanedicarboxylic acid-di-tert-butyl ester 4.29 g (10 mmol) of the trifluoroacetyl derivative produced under Example 1b) is dissolved in 30 ml of ethanol and mixed with 800 mg (20 mmol) of sodium hydroxide solution in 10 ml of distilled water. It is stirred for 3 hours at room temperature, evaporated to dryness in a vacuum at 40° C. bath temperature, water residues are removed by azeotropic distillation with isopropanol and taken up in 30 ml of dimethylformamide. Then, 6.9 g (50 mmol) of potassium carbonate as well as 9.7 g (50 mmol) of bromoacetic acid-tert-butyl ester are added to it and the 4-benzyloxycarbonyl-1,4,7-triazaheptane is alkylated at room temperature overnight. The dimethylformamide is then drawn off in an oil pump vacuum, the residue is dispersed between water and dichloromethane, the organic solution is dried on sodium sulfate, evaporated to dryness in a vacuum and the residue is purified by chromatography on silica gel. The title compound is eluted with ethyl acetate/hexane. It is obtained as foam.

Yield: 6.49 g (93.6% of theory) Elementary analysis: Cld: C 62.32 H 8.57 N 6.06 Fnd: C 62.41 H 8.66 N 6.01 d) 3,9-Bis(tert-butoxycarbonylmethyl)-3,6,9-triazaundecanedicarboxylic acid-di-tert-butyl ester 3.5 g (5 mmol) of the compound produced under Example 1c) is dissolved in 100 ml of ethanol, mixed with 200 mg of Pearlman's catalyst (Pd 20% on activated carbon) and hydrogenated until the calculated amount of hydrogen is taken up. It is suctioned off from the catalyst and evaporated to dryness in a vacuum. The title compound is obtained as white foam.

Yield: 2.80 g (99.9% of theory) Elementary analysis: Cld: C 60.08 H 9.54 N 7.51 Fnd: C 60.02 H 9.62 N 7.56 e) 3,9-Bis(tert-butoxycarbonylmethyl)-6-(2-methyl)-ethoxycarbonylmethyl-3,6,9-triazaundecanedioic acid-di-tert- butyl ester 5.60 g (10 mmol) of the amino compound produced under Example 1d) is dissolved in 30 ml of dimethylformamide. Then, 1.66 g (12 mmol) of potassium carbonate as well as 2.17 g (12 mmol) of 2-bromopropionic acid ethyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 4.18 g (63.4% of theory) Elementary analysis: Cld: C 60.07 H 9.32 N 6.37 Fnd: C 60.18 H 9.40 N 6.31 f) 3,9-Bis(tert-butoxycarbonylmethyl)-6-(2-methyl)-carboxymethyl-3,6,9-triazaundeeanedioie acid-di-tert-butyl ester 6.60 g (10 mmol) of the compound produced under Example 1e) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions in butanol are taken up and evaporated to dryness again in a vacuum. The residue is extracted with toluene. The organic solution is evaporated to dryness in a vacuum and the title compound is obtained as foam.

Yield: 5.35 g (84.7% of theory) Elementary analysis: Cld: C 58.93 H 9.09 N 6.65 Fnd: C 59.01 H 9.16 N 6.60

Example 2

3,9-Bis(tert-butoxycarbonylmethyl)-6-(2-benzyl)-carboxymethyl-3,6,9-triazaundecanedioic acid-di-tert-butyl ester a) 1,7-Bis)benzyloxycarbonyl)-1,4,7-triazaheptane 4.87 g (47.2 mmol) of 1,4,7-triazaheptane as well as 5 ml of triethylamine are dissolved in 100 ml of dichloroethane. The solution of 15.22 g (94.4 mmol) of cyanobenzyl formate in 200 ml of dichloromethane is instilled in this solution within 3 hours. It is allowed to stir for 2 more days at room temperature, then evaporated to dryness in a vacuum, taken up in diethyl ether and washed with sodium bicarbonate solution. The ether solution is dried on sodium sulfate and evaporated to dryness in a vacuum. The residue is crystallized from a little ethanol. The title compound crystallizes into white needles.

Yield: 11.46 g (65.7% of theory) Melting point: 73°–75° C. Elementary analysis: Cld: C 64.67 H 6.78 N 11.31 Fnd: C 64.82 H 6.64 N 11.28 b) 1,7-Bis(benzyloxycarbonyl)-4-trifluoroacetyl-1,4,7-triazaheptane

Analogously to Example 1a), 37.14 g (100 mmol) of the amino compound produced under Example 2a is reacted with 15.63 g (110 mmol) of trifluoroacetic acid ethyl ester in 100 ml of tetrahydrofuran and worked up. The title compound is obtained as oil.

Yield: 43.57 g (93.2% of theory) Elementary analysis: Cld: C 56.53 H 5.18 F 12.19 N 8.99 Fnd: C 56.60 H 5.24 F 12.14 N 9.04 c) 3,9-Bis(tert-butoxycarbonylmethyl)-6-trifluoroacetyl-3,6,9-triazaundecanedioic acid-di-tert-butyl ester Analogously to Example 1d), 4.675 g (10 mmol) of the trifluoroacetyl compound, produced under. Example 5f), in 100 ml of ethanol is hydrogenated with 0.5 g of Pearlman's catalyst (Pd 20%, C) to 4-trifluoroacetyl-1,4,7-triazaheptane and worked up. The amino compound is then alkylated according to Example 1e) in 30 ml of dimethylformamide with 9.7 g (50 mmol) of bromoacetic acid-tert-butyl ester in the presence of 6.9 g (50 mmol) of potassium carbonate. The working-up and purification of the rifle compound also takes place analogously to 5c).

Yield: 5.88 g (89.6% of theory) Elementary analysis: Cld: C 54.95 H 7.99 F 8.69 N 6.41 Fnd: C 54.90 H 8.05 F 8.62 N 6.36 d) 3,9-Bis(tert-butoxycarbonylmethyl)-3,6,9-triazaundecanedicarboxylic acid-di-tert-butyl ester Analogously to Example 1c), 6.57 g (10 mmol) of the trifluoroacetyl compound, produced under Example 2c), in 50 ml of ethanol is dissolved and saponified with 400 mg (100 mmol) of sodium hydroxide solution. It is concentrated by evaporation, the amino compound is taken up in warm toluene, washed with a little water, dried on sodium sulfate and evaporated to dryness in a vacuum. The title compound is obtained as foam.

Yield: 5.24 g (93.6% of theory) Elementary analysis: Cld: C 60.08 H 9.54 N 7.51 Fnd: C 60.02 H 9.48 N 7.44 e) 3,9-Bis(tert-butoxycarbonylmethyl)-6-(2-benzyl)-ethoxycarbonylmethyl-3,6,9-triazaundecanedioic acid-di-tert- butyl ester 5.60 g (10 mmol) of the amino compound produced under Example 2d) is dissolved in 30 ml of dimethylformamide. Then, 1.66 g (12 mmol) of potassium carbonate as well as 3.0 g (12 mmol) of 2-bromophenylpropionic acid ethyl ester are added to it at room temperature and stirred overnight. It is then poured on ice water, extracted with ethyl acetate, the organic solution is dried on sodium sulfate, evaporated to dryness in a vacuum, and the tide compound is obtained by chromatography on silica gel. A mixture of ethyl acetate/hexane is used as eluant.

Yield: 4.30 g (58.4.% of theory) Elementary analysis: Cld: C 64.65 H 9.00 N 5.95 Fnd: C 64.62 H 9.07 N 5.90 f) 3,9-Bis(tert-butoxycarbonylmethyl)-6-(2-benzyl)-carboxymethyl-3,6,9-triazaundecanedioic acid-di-tert-butyl ester 7.06 g (10 mmol) of the compound produced under Example 2e) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions in butanol are taken up and evaporated to dryness again in a vacuum. The residue is extracted with toluene. The organic solution is evaporated to dryness in a vacuum and the title compound is obtained as foam.

Yield: 6.03 g (85.2% of theory) Elementary analysis: Cld: C 63.79 H 8.77 N 6.20 Fnd: C 63.68 H 8.83 N 6.26

Example 3

3,9-Bis(tert-butoxycarbonylmethyl)-6-(2-isopropyl)-carboxymethyl-3,6,9-triazaundecanedioic acid-di-tert-butyl ester a) 1,7-Bis(trifluoroacetyl)-4-benzyl-1,4,7-triazaheptane 29.52 g (100 mmol) of the bis(trifluoroacetyl) compound produced under Example 1a) is dissolved in 200 ml of dimethylformamide. Then, 16.6 g (120 mmol) of potassium carbonate as well as 20.53 g (120 mmol) of benzyl bromide are added to it at room temperature and stirred overnight. Then, it is diluted with 500 ml of diethyl ether, suctioned off from the salts, the ether is drawn off in a vacuum and then concentrated by evaporation in an oil pump vacuum to 50 ml. It is diluted with 600 ml of diethyl ether, poured on ice water and the organic solution is taken up, dried on sodium sulfate, evaporated to dryness in a vacuum and the title compound is obtained by chromatography on silica gel. A mixture of ethyl acetate/hexane is used as eluant.

Yield: 317.50 g (82.4% of theory) Elementary analysis: Cld: C 46.76 H 4.45 F 29.58 N 10.91 Fnd: C 46.83 H 4.51 F 29.50 N 10.87 b) 3,9-Bis(tert-butoxycarbonylmethyl)-6-benzyl-3,6,9-triazaundecanedicarboxylic acid-di-tert-butyl ester 38.53 g (100 mmol) of the trifluoroacetyl derivative produced under 3a) is dissolved in 300 ml of ethanol and mixed with 8 g (200 mmol) of sodium hydroxide solution in 100 ml of distilled water. It is stirred for 3 hours at room temperature, evaporated to dryness in a vacuum at 50° C. bath temperature, water residues are removed by azeotropic distillation with isopropanol and taken up in 300 ml of dimethylformamide. Then, 69 g (500 mmol) of potassium carbonate as well as 97 g (500 mmol) of bromoacetic acid-tert-butyl ester are added to it and the 4-benzyl-1,4,7-triazaheptane is alkylated at room temperature overnight. Then, the dimethylformamide is dram off in an oil pump vacuum, the residue is dispersed between water and dichloromethane, the organic solution is dried on sodium sulfate, evaporated to dryness in a vacuum and the residue is purified by chromatography on silica gel. The title compound is eluted with ethyl acetate/hexane. It is obtained as foam.

Yield: 59.85 g (92.1% of theory) Elementary analysis: Cld: C 64.69 H 9.15 N 6.47 Fnd: C 64.75 H 9.23 N 6.44 c) 3,9-Bis(tert-butoxycarbonylmethyl)-3,6,9-triazaundecanedicarboxylic acid-di-tert-butyl ester 6.50 g (10 mmol) of the compound produced under 3b) is dissolved in 100 ml of ethanol, mixed with 400 mg of Pearlman's catalyst (Pal 20%, C) and hydrogenated until 224 ml of hydrogen is taken up. It is suctioned off from the catalyst, rewashed with ethanol and evaporated to dryness in a vacuum. The title compound is obtained as white foam.

Yield: 5.58 g (99.5% of theory) Elementary analysis: Cld: C 60.08 H 9.54 N 7.51 Fnd: C 60.17 H 9.60 N 7.57 d) 3,9-Bis(tert-butoxycarbonylmethyl)-6-(2-isopropyl)-ethoxycarbonylmethyl-3,6,9-triazaundecanedioic acid-di-tert-butyl ester 5.60 g (10 mmol) of the amino compound produced under Example 3c) is dissolved in 30 ml of dimethylformamide. Then, 1.66 g (12 mmol) of potassium carbonate as well as 2.0 g (12 mmol) of 2-bromo-2-isopropylacetic acid ethyl ester are added to it and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 4.07 g (59.2% of theory) Elementary analysis: Cld: C 61.11 H 9.52 N 6.11 Fnd: C 61.03 H 9.60 N 6.17 e) 3,9-Bis(tert-butoxycarbonylmethyl)-6-(2-isopropyl)-carboxymethyl-3,6,9-triazaundecanedioic acid-di-tert-butyl ester 6.88 g (10 mmol) of the compound produced under Example 3d) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions in butanol are taken up and evaporated to dryness again in a vacuum. The residue is extracted with toluene. The organic solution is evaporated to dryness in a vacuum and the title compound is obtained from hexane.

Yield: 5.53 g (83.8% of theory) Elementary analysis: Cld: C 60.07 H 9.32 N 6.37 Fnd: C 60.18 H 9.41 N 6.44

Example 4

3,9-Bis(tert-butoxycarbonylmethyl)-6-(2-phenyl)-carboxymethyl-3,6,9-triazaundecanedioic acid-di-tert-butyl ester a) 1,7-Bis(phthalimido)-4-benzyl-1,4,7-triazaheptane 36.34 g (100 mmol) of 1,7-bis(phthalimido)-1,4,7-triazaheptane [produced according to J. Org. Chem. USSR, 23:3302 (1987)] is dissolved in 500 ml of dimethylformamide. Then, 16.6 g (120 mmol) of potassium carbonate as well as 20.53 g (120 mmol) of benzyl bromide are added to it and stirred overnight at 25° C. It is poured in ice water, the precipitated product is suctioned off, rewashed with water, taken up in 1,2-dichloroethane, dried on sodium sulfate and evaporated to dryness in a vacuum. The title compound is obtained as solid.

Yield: 42.76 g (94.3% of theory) Elementary analysis: Cld: C 71.51 H 5.11 N 9.27 Fnd: C 71.40 H 5.18 N 9.38 b) 3,9-Bis(tert-butoxycarbonylmethyl)-6-benzyl-3,6,9-triazaundecanedioicacid-di-tert-butyl ester 22.68 g (50 mmol) of the compound produced under 4a) is added in portions with stirring in 250 ml of hydrazine hydrate. It is heated for 4 more hours to 60° C., allowed to cool off, suctioned off from phthalhydrazide, rewashed with hydrazine hydrate and concentrated by evaporation in a vacuum. The residue is freed from hydrazine residues by codistillation with isopropanol. The 4-benzyl-1,4,7-triazaheptane in 150 ml of dimethylformamide is taken up, 34.5 g (250 mmol) of potassium carbonate is added to it and finally 48.5 g (250 mmol) of bromoacetic acid-tert-butyl ester. The alkylation is allowed to be in progress overnight at room temperature. Then, the dimethylformamide is drawn off in an oil pump vacuum, the residue is dispersed between water and dichloromethane, dried on sodium sulfate, evaporated to dryness in a vacuum and the residue is purified by chromatography on silica gel. The title compound is obtained as foam.

Yield: 51.15 g (78.7% of theory) Elementary analysis: Cld: C 64.69 H 9.15 N 6.47 Fnd: C 64.60 H 9.20 N 6.53 c) 3,9-Bis(tert-butoxycarbonylmethyl)-3,6,9-triazaundecanedicarboxylic acid-di-tert-butyl ester 13.0 g (20 mmol) of the compound produced under 4b) is dissolved in 200 ml of ethanol, mixed with 0.8 g of Pearlman's catalyst (Pd 20%, C) and hydrogenated until 448 ml of hydrogen is taken up. It is suctioned off from the catalyst, rewashed with ethanol and evaporated to dryness in a vacuum. The title compound is obtained as foam.

Yield: 5.52 g (98.7% of theory) Elementary analysis: Cld: C 60.08 H 9.54 N 7.51 Fnd: C 60.01 H 9.62 N 7.58 d) 3,9-Bis(tert-butoxycarbonylmethyl)-6-(2-phenyl)-methoxycarbonylmethyl-3,6,9-triazaundecanedioic acid-di-tert-butyl ester 5.60 g (10 mmol) of the amino compound produced under Example 4c) is dissolved in 30 ml of dimethylformamide. Then, 1.66 g (12 mmol) of potassium carbonate as well as 2.22 g (12 mmol) of 2-chlorophenylacetic acid methyl ester are added to it and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 4.40 g (62.1% of theory) Elementary analysis: Cld: C 62.78 H 8.69 N 5.94 Fnd: C 62.89 H 8.76 N 5.88 e) 3,9-Bis(tert-butoxycarbonylmethyl)-6-(2-phenyl)-carboxymethyl-3,6,9-triazaundecanedioic acid-di-tert-butyl ester 7.08 g (10 mmol) of the compound produced under Example 4d) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol, and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions in butanol are taken up and evaporated to dryness again in a vacuum. The residue is extracted with toluene. The organic solution is evaporated to dryness in a vacuum and the title compound is obtained as foam.

Yield: 5.99 g (86.3% of theory) Elementary analysis: Cld: C 62.32 H 8.57 N 6.06 Fnd: C 62.40 H 8.65 N 6.02

Example 5

3,9-Bis(tert-butoxycarbonylmethyl)-6-[2-(4-methoxyphenyl)]-carboxymethyl-3,6,9-triazaundecanedioic acid-di-tert-butyl ester a) 2-Bromo-2-(4-methoxyphenyl)-acetic acid methyl ester 27.01 g (169 mmol) of bromine is added with intensive stirring to a mixture of 18.46 g (100 mmol) of 2-(4-methoxyphenyl)-acetic acid chloride and 1.24 g (40 mmol) of red phosphorus, so that the bromine coloring fades away steadily. After about half the amount of bromine is added, it is heated for 3 more hours at 40° C. 4.49 g (140 mmol) of methanol is then instilled in the cooled solution, it is allowed to stir for one more hour, diluted with 100 ml of dichloromethane, the solution is instilled with intensive stirring in ice water, the organic phase is separated, washed with saturated sodium carbonate solution and dried on sodium sulfate and evaporated to dryness in a vacuum. The residue is purified by distillation in the bulb tube in the oil pump vacuum.

Yield: 19.59 g (75.6% of theory) Elementary analysis: Cld: C 46.36 H 4.28 Br 30.84 Fnd:. C 46.42 H 4.35 Br 30.78 b) 3,9-Bis(tert-butoxycarbonylmethyl)-6-[2-(4-methoxyphenyl)]-methoxy-carbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 3.11 g (12 mmol) of 2-bromo-2-(4-methoxyphenylacetic acid methyl ester) are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 5.50 g (74.6% of theory) Elementary analysis: Cld: C 61.85 H 8.60 N 5.69 Fnd: C 61.78 H 8.66 N 5.75 c) 3,9-Bis(tert-butoxycarbonylmethyl)-6-[2-(4-methoxyphenyl)]-carboxylmethyl-3,6,9-triazaundecanedioic acid-di-tert-butyl ester 7.38 g (10 mmol) of the compound produced under Example 5b) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions in butanol are taken up and evaporated to dryness again in a vacuum. The residue is extracted with toluene. The organic solution is evaporated to dryness in a vacuum and the title compound is obtained as foam.

Yield: 6.39 g (88.3% of theory) Elementary analysis: Cld: C 61.39 H 8.49 N 5.80 Fnd: C 61.31 H 8.56 N 5.74

Example 6

3,9-Bis(tert-butoxycarbonylmethyl)-6-[2-(4-ethoxybenzyl)-carboxymethyl-3,6,9-triazaundecanedioic acid-di-tert-butyl ester 2-Bromo-3-(4-ethoxyphenyl)-propionic acid ethyl ester a) 3-(4-Ethoxyphenyl)-propionic acid 16.62 g (100 mmol) of 3-(4-hydroxyphenyl)-propionic acid is dissolved with stirring and covering with argon in 45 ml (225.0 mmol) of 5 N sodium hydroxide solution, and 15.73 g (100 mmol), (98%) of diethyl sulfate is instilled quickly so that the temperature does not exceed 40° C. (water cooling). After completion of the addition, it is heated for 30 more minutes to 100° C. After the cooling, it is extracted with diethyl ether, then acidified with sulfuric acid to pH 4 and the precipitated compound in ether is taken up. After drying on sodium sulfate, it is evaporated to dryness in a vacuum. The title compound is obtained as solid.

Yield: 15.21 g (78.3% of theory) Elementary analysis: Cld: C 68.02 H 7.26 Fnd: C 68.13 H 7.34 b) 2-Bromo-3-(4-ethoxyphenyl)-propionic acid ethyl ester

A drop of dimethylformamide is added to 9.71 g (50 mmol) of the acid, produced under 6a), in 50 ml of 1,2-dichloroethane. Then, it is heated to 80° C. and 5.0 ml (68.6 mmol) of thionyl chloride is instilled in it. Vigorous gas generation takes place. After completion of the addition, it is refluxed for one more hour, then evaporated to dryness in a vacuum and 0.62 g (20 mmol) of red phosphorus is added to the acid chloride. Then, 13.6 g (85 mmol) of bromine is quickly instilled with stirring so that the bromine coloring simply fades away. When about half the amount of bromine is added, it is heated to 40° C. and the temperature is maintained for three hours. It is cooled to room temperature and then 3.22 g (70 mmol) of ethanol in 20 ml of dichloromethane is instilled in it. After one hour, it is diluted with 200 ml of dichloromethane, poured on ice water, the organic solution is separated, washed with saturated sodium bicarbonate solution and evaporated to dryness in a vacuum. The title compound is purified by chromatography on silica gel. A mixture of ethyl acetate and hexane is used as eluant. The title compound is obtained as syrup.

Yield: 11.57 g (76.8% of theory) Elementary analysis: Cld: C 51.84 H 5.69 Br 26.53 Fnd: C 51.77 H 5.74 Br 26.59 c) 3,9-Bis(tert-butoxycarbonylmethyl)-6-[2-(4-ethoxybenzyl)-ethoxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 3.61 g (12 mmol) of 2-bromo-2-(4-ethoxybenzyl)-acetic acid ethyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 4.95 g (63.4% of theory) Elementary analysis: Cld: C 63.13 H 8.92 N 5.39 Fnd: C 63.07 H 8.89 N 5.44 d) 3,9-Bis(tert-butoxycarbonylmethyl)-6-[2-(4-ethoxybenzyl)-carboxymethyl-3,6,9-triazaundecanedioic acid-di-tert-butyl ester 7.80 g (10 mmol) of the compound produced under Example 6c) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions in butanol are taken up and evaporated to dryness again in a vacuum. The residue is extracted with toluene. The organic solution is evaporated to dryness in a vacuum and the title compound is obtained as foam.

Yield: 6.47 g (86.1% of theory) Elementary analysis: Cld: C 62.29 H 8.71 N 5.59 Fnd: C 62.36 H 8.77 N 5.57

Example 7

3,9-Bis(tert-butoxycarbonylmethyl)-6-[2-(pyrid-2-yl)]-ethoxycarbonylmethyl-3,6,9-triazaundecanedioic acid-di-tert-butyl ester a) 2-Bromo-2-(pyrid-2-yl)-acetic acid ethyl ester 16.52 g (100 mmol) of 2-pyridylacetic acid ethyl ester is dissolved in 50 ml of carbon tetrachloride. It is cooled to 0° C. and 15.98 g (100 mmol) of bromine, dissolved in 15 ml of carbon tetrachloride, is then instilled in it within 30 minutes. Then, it is allowed to react for one more hour at 25° C. The bromine coloring fades away. It is concentrated by evaporation in a vacuum and obtains the hydrobromide of the title compound. The free compound is obtained by extraction of ether from the aqueous solution after adding sodium bicarbonate.

Yield: 22.80 g (93.4% of theory) Elementary analysis: Cld: C 44.29 H 4.13 Br 32.74 N 5.74 Fnd: C 44.22 H 4.18 Br 32.81 N 5.68 b) 3,9-Bis(tert-butoxycarbonylmethyl)-6-[2-(pyrid-2-yl)]-ethoxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 2.93 g (12 mmol) of 2-bromo-2-(pyrid-2-yl)-acetic acid ethyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 5.11 g (69.2% of theory) Elementary analysis: Cld: C 60.14 H 8.46 N 7.58 Fnd: C 60.21 H 8.55 N 7.66 c) 3,9-Bis(tert-butoxycarbonylmethyl)-6-[2-(pyrid-2-yl)]-carboxymethyl-3,6,9-triazaundecanedioic acid-di-tert-butyl ester 7.39 g (10 mmol) of the compound produced under Example 7b) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions in butanol are taken up and evaporated to dryness again in a vacuum. The residue is extracted with toluene. The organic solution is evaporated to dryness in a vacuum and the title compound is obtained as foam.

Yield: 5.96 g (87.6% of theory) Elementary analysis: Cld: C 61.74 H 6.59 N 6.17 Fnd: C 61.66 H 6.65 N 6.24

Example 8

3,9-Bis(tert-butoxycarbonylmethyl)-6-[2-(2,5-dioxahexyl)]-carboxymethyl-3,6,9-triazaundecanedioic acid-di-tert-butyl ester a) 4,7-Dioxaoctanoic acid benzyl ester 1.15 g (50.0 mmol) of sodium is dissolved in 100 ml of dried ethylene glycol monomethyl ether. Then, 5.01 g (50 mmol) of freshly distilled ethyl acrylate, dissolved in 15 ml of dried diethyl ether at 0° C., is instilled in it with stirring and exclusion of moisture. It is allowed to stir for 1 more hour at the low temperature, then 5 ml of water is added to it and heated for 2 hours to 60° C. to saponify the ester. It is concentrated by evaporation in a vacuum to 30 ml, diluted with 100 ml of water, the solution is extracted with ether and then the aqueous phase is adjusted with sulfuric acid to pH 4. The precipitated compound in diethyl ether is taken up, the solution is dried on sodium sulfate and evaporated to dryness in a vacuum. The title compound is obtained as syrup.

Yield: 6.11 g (82.5% of theory) Elementary analysis: Cld: C 48.64 H 8.16 Fnd: C 48.71 H 8.23 b) 2-Bromo-4,7-dioxaoctanoic acid benzyl ester

One drop of dimethylformamide is added to 7.41 g (50 mmol) of the acid, produced under Example 8a), in 50 ml of 1,2-dichloroethane. Then, it is heated to 80° C. and 5.0 ml (68.6 mmol) of thionyl chloride is instilled in it. Vigorous gas generation takes place. After completion of the addition, it is refluxed for one more hour and then evaporated to dryness in a vacuum. 0.62 g (20 mmol) of red phosphorus is added to the acid chloride and then 13.6 g (85 mmol) of bromine is quickly instilled with stirring so that the bromine coloring simply fades away. When about half the mount of bromine is added, it is heated to 40° C. and this temperature is maintained for three more hours. It is cooled to room temperature and the mixture of 7.57 g (70 mmol) of benzyl alcohol and 7.08 g (70 mmol) of dry triethylamine in 20 ml of dichloromethane is instilled in it. After 1 hour, it is diluted with 200 ml of dichloromethane, poured on ice water and the organic solution is separated. It is washed with saturated sodium bicarbonate solution, dried on sodium sulfate and evaporated to dryness in a vacuum. The title compound is purified by chromatography on silica gel. A mixture of ethyl acetate and hexane is used as eluant. The title compound is obtained as syrup.

Yield: 12.43 g (78.4% of theory) Elementary analysis: Cld: C 49.23 H 5.40 Br 25.19 Fnd: C 49.30 H 5.46 Br 25.10 c) 3,9-Bis(tert-butoxycarbonylmethyl)-6-[2-(2,5-dioxahexyl)]-benzyloxy-carbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 3.81 g (12 mmol) of 2-bromo-4,7-dioxaoctanoic acid benzyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 5.20 g (65.2% of theory) Elementary analysis: Cld: C 61.79 H 8.85 N 5.27 Fnd: C 61.87 H 8.92 N 5.22 d) 3,9-Bis(tert-butoxycarbonylmethyl)-6-[2-(2,5-dioxahexyl)]-carboxymethyl-3,6,9-triazaundecanedioic acid-di-tert-butyl ester 7.97 g (10 mmol) of the benzyl ester produced under 8c) is dissolved in 100 ml of ethanol and mixed with 0.4 g of Pearlman's catalyst (Pd 20%, C). It is hydrogenated until 224 ml of hydrogen is taken up, then suctioned off from the catalyst, washed well with ethanol and the solution is evaporated to dryness in a vacuum. The product is obtained as foam.

Yield: 6.87 g (97.3% of theory) Elementary analysis: Cld: C 57.85 H 9.00 N 5.95 Fnd: C 57.91 H 9.11 N 6.01

Example 9

3,9-Bis(tert-butoxycarbonylmethyl)-6-(2-hydroxymethyl)-carboxymethyl-3,6,9-triazaundecanedioic acid-di-tert-butyl ester a) 3-Benzyloxy-2-bromopropionic acid methyl ester 40.3 g (339 mmol) of potassium bromide is dissolved in 200 ml of 2.5N sulfuric acid. 19.52 g (100 mmol) of 3-benzyloxy-serine is added to it, cooled to 0° C. and 10.6 g (154 mmol) of sodium nitrite is added in the course of one hour with vigorous stirring. It is allowed to stir for one more hour at 0° C. and for another at 25° C. Then, it is extracted with ether, the solution is washed with water, dried on sodium sulfate and the carboxylic acid is esterified by adding an ethereal diazomethane solution in portions until the reaction is discernibly completed (coloring, TLC control). The solution is concentrated by evaporation in a vacuum. The title compound is purified by chromatography on silica gel with a mixture of ether and hexane as eluant. It is obtained as oil.

Yield: 22.97 g (84.1% of theory) Elementary analysis: Cld: C 48.37 H 4.80 Br 29.26 Fnd: C 48.30 H 4.86 Br 29.33 b) 3,9-Bis(tert-butoxycarbonylmethyl)-6-[2-(benzyloxymethyl)]-ethoxy-carbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 3.28 g (12 mmol) of 2-bromo-3-benzyloxypropionic acid benzyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 5.09 g (67.1% of theory) Elementary analysis: Cld: C 63.39 H 7.85 N 5.54 Fnd: C 63.51 H 7.90 N 5.59 c) 3,9-Bis(tert-butoxycarbonylmethyl)-6-(2-hydroxymethyl)-carboxymethyl-3,6,9-triazaundecanedioic acid-di-tert-butyl ester 7.52 g (10 mmol) of the benzyl ether produced under 9b) is dissolved in 100 ml of ethanol and mixed with 0.4 g of Pearlman's catalyst (Pd 20%, C). It is hydrogenated until 224 mi of hydrogen is taken up, then suctioned off from the catalyst, rewashed well with ethanol and evaporated to dryness in a vacuum. The product is obtained as foam.

Yield: 5.71 g (88.1% of theory) Elementary analysis: Cld: C 57.48 H 8.87 N 6.49 Fnd: C 57.60 H 8.98 N 6.59

Example 10

3,9-Bis(tert-butoxycarbonylmethyl)-6-[2-(4-benzyloxycarbonylamino)-butyl]-carboxymethyl-3,6,9-triazaundecanedioic acid-di-tert-butyl ester a) 3,9-Bis(tert-butoxycarbonylmethyl)-6-[2-(4-bromo)-butyl]-ethoxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 3.62 g (12 mmol) of 2,6-dibromohexanoic acid ethyl ester are added to it at room temperature and stirred overnight. It is then poured on ice water, extracted with ethyl acetate, the organic solution is dried on sodium sulfate, evaporated to dryness in a vacuum and the rifle compound is obtained by chromatography on silica gel. A mixture of ethyl acetate/hexane is used as eluant.

Yield: 4.90 g (62.7% of theory) Elementary analysis: Cld: C 55.38 H 8.52 Br 10.23 N 5.38 Fnd: C 55.48 H 8.59 Br 10.34 N 5.31 b) 3,9-Bis(tert-butoxycarbonylmethyl)-6-[2-(4-benzyloxycarbonylamino)-butyl]-carboxymethyl-3,6,9-triazaundecanedioic acid-di-tert-butyl ester 7.81 g (10 mmol) of the compound produced under Example 10a) is dissolved in 50 ml of nitromethane and mixed with 1.56 g (10.4 mmol) of silver cyanate. It is stirred with exclusion of moisture for 70 hours at room temperature. Then, it is mixed with 1.62 g (15 mmol) of benzyl alcohol and allowed to stir for another 3 hours at room temperature. Then, it is diluted with 200 ml of diethyl ether, filtered off from silver salt, the solution is concentrated by evaporation in a vacuum and the residue is purified by column chromatography on silica gel. A mixture of ethyl acetate and hexane is used as eluant. The title compound is obtained as amorphous foam.

Yield: 5.84 g (68.6% of theory) Elementary analysis: Cld: C 62.10 H 8.76 N 6.58 Fnd: C 62.23 H 8.83 N 6.67

Example 11

3,9-Bis(tert-butoxycarbonylmethyl)-6-carboxymethyl-3,6,9-triazaundecanedioicacid-di-tert-butyl ester a) 3,9-Bis(tert-butoxycarbonylmethyl)-6-benzyloxycarbonylmethyl-3,6,9-triazaundecanedioic acid-di-tert-butyl ester 5.60 g (10 mmol) of the amino compound produced under Example 1d) is dissolved in 30 ml of dimethylformamide. Then, 1.66 g (12 mmol) of potassium carbonate as well as 2.58 g (12 mmol) of 2-bromoacetic acid benzyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 6.32 g (89.3% of theory) Elementary analysis: Cld: C 64.65 H 9.00 N 5.95 Fnd: C 64.62 H 9.07 N 5.90 b) 3,9-Bis(tert-butoxycarbonylmethyl)-6-carboxy-methyl-3,6,9-triazaundecanedioic acid-di-tert-butyl ester 7.08 g (10 mmol) of the benzyl ester produced under 11a) is dissolved in 100 ml of ethanol and mixed with 0.4 g of Pearlman's catalyst (Pal 20%, C). It is hydrogenated until 224 ml of hydrogen is taken up, suctioned off from the catalyst, rewashed well with ethanol and the solution is evaporated to dryness in a vacuum. The product is obtained as foam, which crystallized from ether/hexane.

Yield: 6.87 g (97.3% of theory) Melting point: 73°–75° C. Elementary analysis: Cld: C 57.85 H 9.00 N 5.95 Fnd: C 57.91 H 9.11 N 6.01

Example 12

3,9-B is(tert-butoxycarbonylmethyl)-6-(2-phenyl)-carboxymethyl-3,6,9-triazaundecanedicarboxylic acid-di-tert-butyl ester a) 3,9-Bis(tert-butoxycarbonylmethyl)-6-(2-phenyl)-ethoxycarbonylmethyl-3,6,9-triazaundecanedioic acid 5.60 g (10 mmol) of the amino compound produced under Example 1d) is dissolved in 30 ml of dimethylformamide. Then, 1.66 g (12 mmol) of potassium carbonate as well as 2.00 g (12 mmol) 3.60 g (12 mmol) of 2-trifluoromethylsulfonylphenylacetic acid ethyl ester are added to it at room temperature and stirred overnight. It is then poured on ice water, extracted with ethyl acetate, the organic solution is dried on sodium sulfate, evaporated to dryness in a vacuum and the title compound is obtained by chromatography on silica gel. A mixture of ethyl acetate/hexane is used as eluant.

Yield: 6.23 g (86.3% of theory) Elementary analysis: Cld: C 63.23 H 8.80 N 5.82 Fnd: C 63.11 H 8.89 N 5.76 b) 3,9-Bis(tert-butoxycarbonylmethyl)-6-(2-phenyl)-carboxymethyl-3,6,9-triazaundecanedioic acid-di-tert-butyl ester 6.60 g (10 mmol) of the compound produced under Example 12a) is dissolved in 50 ml of ethanol. The solution of 400 mg (10 mmol) of sodium hydroxide in 5 ml of distilled water is then added to it and stirred for 3 hours at 50° C. According to the thin-layer chromatogram, saponification is quantitative. It is evaporated to dryness in a vacuum, traces of water are removed by codistillation with ethanol and the residue is dried at 40° C. in a vacuum. The title compound is obtained as white powder. The remaining white residue is dissolved in 80 ml of wet ethanol (9:1) and mixed with stirring with the solution of 535 mg (10 mmol) of ammonium chloride in 10 ml of distilled water. It is evaporated to dryness in a vacuum, the soluble portions in butanol are taken up and evaporated to dryness again in a vacuum. The residue is extracted with toluene. The organic solution is evaporated to dryness in a vacuum and the title compound is obtained as foam.

Yield: 6.02 g (86.7% of theory) Elementary analysis: Cld: C 63.79 H 8.77 N 6.20 Fnd: C 63.68 H 8.83 N 6.26

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. An ester selected from the group consisting of [3,9-Bis(tert-butoxycarbonylmethyl)-6-carboxymethyl-3,6,9]3,9-bis(tert-butoxycarbonyl-methyl)-6-carboxymethyl-3,6,9 triazaundecanedioic acid-di-tert-butyl ester, 3,9-bis(tert-butoxycarbonylmethyl)-6-(2-methyl)-carboxymethyl-3,6,9-triazaundecanedioic acid-di-tert-butyl ester, 3,9-bis(tert-butoxycarbonylmethyl)-6-(2-ethyl)-carboxymethyl-3,6,9-triazaundecanedioic acid-di-tert-butyl ester, 3,9-bis(tert-butoxycarbonylmethyl)-6-(2-propyl)-carboxymethyl-3,6,9-triazaundecanedioic acid-di-tert-butyl ester, 3,9-bis(tert-butoxycarbonylmethyl)-6-(2-isopropyl)-carboxymethyl-3,6,9-triazaundecanedioic acid-di-tert-butyl ester, 3,9-bis(tert-butoxycarbonylmethyl)-6-(2-butyl)-carboxymethyl-3,6,9-triazaundecanedioic acid-di-tert-butyl ester, 3,9-bis(tert-butoxycarbonylmethyl)-6-(2-isobutyl)-carboxymethyl-3,6,9-triazaundecanedioic acid-di-tert-butyl ester, 3,9-bis(tert-butoxycarbonylmethyl)-6-(2-tert-butyl)-carboxymethyl-3,6,9-triazaundecanedioic acid-di-tert-butyl ester, 3,9-bis(tert-butoxycarbonylmethyl)-6-(2-pentyl)-carboxymethyl-3,6,9-triazaundecanedioic acid-di-tert-butyl ester, 3,9-bis(tert-butoxycarbonylmethyl)-6-(2-hexyl)-carboxymethyl-3,6,9-triazaundecanedioic acid-di-tert-butyl ester, 3,9-bis(tert-butoxycarbonylmethyl)-6-(2-cyclohexyl)-carboxymethyl-3,6,9-triazaundecanedioic acid-di-tert-butyl ester, 3,9-bis(tert-butoxycarbonylmethyl)-6-(2-phenyl)-carboxymethyl-3,6,9-triazaundecanedioic acid-di-tert-butyl ester, 3,9-bis(tert-butoxycarbonylmethyl)-6-(2-benzyl)-carboxymethyl-3,6,9-triazaundecanedioic acid-di-tert-butyl ester, 3,9-bis(tert-butoxycarbonylmethyl)-6-(2-hydroxymethyl)-carboxymethyl-3,6,9-triazaundecanedioic acid-di-tert-butyl ester, 3,9-bis(tert-butoxycarbonylmethyl)-6-(2-(1-hydroxyethyl))-carboxymethyl-3,6,9-triazaundecanedioic acid-di-tert-butyl ester, 3,9-bis(tert-butoxycarbonylmethyl)-6-(2-carboxymethyl)-carboxymethyl-3,6,9-triazaundecanedioic acid-di-tert-butyl ester, 3,9-bis(tert-butoxycarbonylmethyl)-6-(2-(2-carboxyethyl))-carboxymethyl-3,6,9-triazaundecanedioic acid-di-tert-butyl ester, 3,9-bis(tert-butoxycarbonylmethyl)-6-(2-(4-aminobutyl))-carboxymethyl-3,6,9-triazaundecanedioic acid-di-tert-butyl ester, 3,9-bis(tert-butoxycarbonylmethyl)-6-(2-mercaptomethyl))-carboxymethyl-3,6,9-triazaundecanedioic acid-di-tert-butyl ester, 3,9-bis(tert-butoxycarbonylmethyl)-6-(2-methylthiomethyl)-carboxymethyl-3,6,9-triazaundecanedioic acid-di-tert-butyl ester, 3,9-bis(tert-butoxycarbonylmethyl)-6-(2-(p-hydroxyphenyl))-carboxymethyl-3,6,9-triazaundecanedioic acid-di-tert-butyl ester, 3,9-bis(tert-butoxycarbonylmethyl)-6-(2-(p-hydroxybenzyl))-carboxymethyl-3,6,9-triazaundecanedioic acid-di-tert-butyl ester and 3,9-bis(tert-butoxycarbonylmethyl)-6-(2-carboxymethyl)-carboxymethyl-3,6,9-triazaundecanedioic acid-di-tert-butyl ester.

* * * * *